United States Patent [19]
Brown et al.

[11] Patent Number: 5,736,141
[45] Date of Patent: Apr. 7, 1998

[54] METHOD TO PREVENT FERTILIZATION IN MAMMALS BY ADMINISTERING A SINGLE DOSE OF ZONA PELLUCIDA DERIVED ANTIGENS, LIPOSOME AND FREUND'S ADJUVANT

[75] Inventors: Robert Brown, Dartmouth; Michael Mezei, Halifax; Bill Pohajdak, Dartmouth; Warwick Charles Kimmins, Halifax, all of Canada

[73] Assignee: Dalhousie University, Canada

[21] Appl. No.: 739,812

[22] Filed: Oct. 30, 1996

Related U.S. Application Data

[63] Continuation of Ser. No. 347,348, Dec. 5, 1994, abandoned, which is a continuation-in-part of Ser. No. 892,807, Jun. 5, 1992, abandoned.

[51] Int. Cl.$^6$ .................. A61K 39/00; A61K 9/127; A61K 35/54
[52] U.S. Cl. .............. 424/184.1; 424/450; 424/559; 424/561; 424/812; 514/21; 530/853
[58] Field of Search ................ 424/450, 184.1, 424/559, 561, 812; 514/21; 530/853

[56] References Cited

U.S. PATENT DOCUMENTS

| | | | |
|---|---|---|---|
| 4,053,585 | 10/1977 | Allison et al. | 424/450 |
| 4,370,349 | 1/1983 | Evans et al. | 514/785 |
| 4,879,213 | 11/1989 | Fox et al. | 435/5 |
| 4,996,297 | 2/1991 | Dunbar | 424/185.1 |
| 5,100,662 | 3/1992 | Bolcsak et al. | 424/450 |

FOREIGN PATENT DOCUMENTS

| | | |
|---|---|---|
| 1504259 | 3/1978 | United Kingdom. |
| 8903399 | 4/1989 | WIPO. |

OTHER PUBLICATIONS

Eldridge, J. L., et al.; Biodegradable Microspheres: Vaccine Delivery System for Oral Immunization; Current Topics in Microbiology and Immunology, 1989, 146, 59–66.
Journal of Biological Chemistry, vol. 262, No. 2, 15 Jan. 1987.
Vaccine Biotechnology, 1989, Academic Press pp. 301–343.
Vaccine Biotechnology, 1989, Academic Press pp. 323–324.
Bowie et al. Science 247:1306–1310 1990.
Sacco et al. Am. J. Reprod. Immunology 21:1–8 1989.
Kumar et al. PNAS 87:1337–1341 1990.
Webster's New World Dictionary, published by the World Publishing Company (1968) see p. 1063.

*Primary Examiner*—Anthony C. Caputa
*Attorney, Agent, or Firm*—Lorusso & Loud

[57] ABSTRACT

A vaccine for the immunocontraception of mammals is described. The vaccine consists of zona pellucida antigens and an adjuvant encapsulated in a liposome delivery system. The liposome delivery system allows for the slow release of antigen resulting in a prolonged immune response. In particular, after a single injection of the vaccine, levels of anti-zona pellucida antibodies were detected for up to 22 months in seals. Thus, the vaccine according to the present invention is effective after a single dose and is therefore very useful in immunocontraceptive protocols.

6 Claims, No Drawings

METHOD TO PREVENT FERTILIZATION IN MAMMALS BY ADMINISTERING A SINGLE DOSE OF ZONA PELLUCIDA DERIVED ANTIGENS, LIPOSOME AND FREUND'S ADJUVANT

This application is a continuation of application Ser. No. number 08/347,348, filed Dec. 5, 1994, now abandoned, which is the national phase of PCT/CA93/00239, filed Jun. 7, 1995, which is a continuation-in-part of U.S. patent application No. 07/892,807, which was filed on Jun. 5, 1992 and is now abandoned.

FIELD OF THE INVENTION

The present invention relates to a vaccine composition for the immunocontraception of mammals.

BACKGROUND OF THE INVENTION

There is a real need for population control in several species of domestic and wild animals. Methods such as surgical sterilization, or more drastically, culling are generally not acceptable or even allowable in most countries. For example, in Canada the culling or harvesting of seals was prohibited in the early 1980's, resulting in an increased seal population from 10,000 in 1978 to approximately 45,000 at present. Increases in harp seal populations have been much greater. Unfortunately, the increasing population of seals is eating away at the diminishing fish stocks which poses serious problems for the fishing industry. The seals also contain parasites such as seal worms that they pass on to the fish. In 1986 it was estimated that the cost to the fishing industry of removing seal worms from fish by hand was upwards of $30 million a year. Therefore, it is highly desirable to develop an effective form of contraception in mammals, such as seals, in order to effectively control the population growth of certain mammals.

One form of contraception for mammals has involved immunocontraception using glycoproteins isolated from the zona pellucida, a covering which surrounds oocytes. The zona pellucida glycoproteins (hereafter referred to as ZP) provide an attachment site for sperm. Immunocontraception with ZP results in the production of antibodies to ZP which cause (a) an alteration of the nature of the ZP membrane of ova, thereby inhibiting sperm entry, (b) an inhibition of implantation of fertilized ova into the uterus and (c) decreased ovarian follicular differentiation (Henderson, C. J., M. J. Hulme and R. J. Aitken. 1988. Contraceptive potential of antibodies to the zona pellucida. J. Reprod. Fert. 83: 325–343). Immunocontraception has been induced with both zona pellucida glycoproteins and epitopes of these glycoproteins which have been sequenced, synthesized and coupled to carrier proteins (Millar, S. E., S. M. Chamow, A. W. Baur, C. Oliver, F. Robey and J. Dean. 1989. Vaccination with a synthetic zona pellucida peptide produces long-term contraception in female mice. Science 246: 935–938). The use of ZP glycoproteins for immunocontraception has several advantages over other contraception methods. Firstly, ZP glycoproteins are unique to the female reproductive system and therefore, anti-ZP antibodies likely have little or no effect on other tissues. Secondly, the infertility caused by anti-ZP antibodies is reversible, although, hyper- immunization may cause permanent sterility.

Previous studies have shown that in order to effect immunocontraception, multiple injections of ZP were necessary (Kirkpatrick, J. F., I. K. M. Liu and J. W. Turner. 1990. Remotely-delivered immunocontraception in feral horses. Wildl. Soc. Bull. 18: 326–330). Multiple injections are clearly not practical for wild populations as it entails recapturing the same wild animal each time an injection is necessary. Multiple injections are also cumbersome in any situation.

Therefore, it is desirable to develop an immunocontraceptive vaccine which would be effective for long periods following a single injection in an efficient delivery system.

Liposomes have been used to carry drugs to sites of inflammation and infection or in some cases tumours. Liposomes are microscopic spheres composed of either a single or multiple concentric bilayer sheets, and range in size from a nanometer to several micrometers in diameter. These bilayer sheets can be formed from a wide variety of phospholipids in varied formulations. Cholesterol can be included in the bilayer in order to increase the bilayer strength and reduce the leakage of materials encapsulated within the entrapped aqueous interior. A vast array of compounds can be associated with liposomes, including small molecules, drugs, proteins, and nucleic acids. Liposome-associated compounds can be encapsulated within the aqueous interior of the liposome (i.e. between the bilayer sheets), integrated into the bilayer, or adsorbed or attached to the bilayer surface. The location depends upon the properties of the associating compounds as well as the procedures used for the formation of the liposome.

A liposome based vaccine system has been described for immunization against human malaria (Fries et al, 1992. Liposomal Malaria Vaccine in humans: A safe and potent adjuvant strategy. Proc. Natl. Acad. Sci. USA. 89: 358–362). In this system, a recombinant malaria protein derived from *Plasmodium falcioarum* was encapsulated into liposomes and injected into male volunteers. However the results indicate that at least three injections of the vaccine were required in order to produce an elevated antibody response.

SUMMARY OF THE INVENTION

The present invention relates to an immunocontraceptive vaccine preparation which comprises zona pellucida antigens incorporated into a liposome delivery system. The liposome system effects the slow release of antigen resulting in an extended period of antibody production and thereby an extended period of contraception. Therefore, the present invention provides a method to achieve immunocontraception of mammals using a single injection of zona pellucida glycoproteins.

Accordingly, the invention provides a vaccine composition for the immunocontraception of a mammal which comprises a zona pellucida derived antigen incorporated into a liposome system.

The invention further provides a vaccine composition capable of inducing the production of antibodies to a zona pellucida antigen, said composition comprising a zona pellucida derived antigen incorporated into a liposome system.

In one embodiment of the present invention, the liposome vaccine composition is freeze-dried and incorporated into a BALLISTIVET biobullet. Such an embodiment makes the vaccine easier to deliver to the animal.

In another aspect, the invention provides a method of preventing fertilization in a mammal which comprises administering an effective amount of the above-described vaccine.

DETAILED DESCRIPTION OF THE INVENTION

Isolation and purification of zona pellucide glycoproteins

Zona pellucidaglycoproteins were isolated and purified as described by Yurewicz (in Yurewicz, E. C., A. G. Sacco, and M. G. Subramanian, Structural Characterization of the Mr=55,000 Antigen (ZP3) of Porcine Oocyte Zona Pellucida, The Journal of Biological Chemistry 262: 564 –571 (1987). Porcine ovaries were homogenized and the oocytes recovered from the homogenate by sieving through nylon screens of decreasing pore size (500, 350, 200, 175, 100 and 40 μm). The oocytes were homogenized with a glass-teflon apparatus and the homogenate was passed through a 40 um screen to collect the fractured zonae. The fractured zonae were washed with buffer and recollected on the 40 um screen. Zona pellucida glycoproteins were solubilized by incubating the zonae in a water bath (73° C. for 20 minutes). The fraction obtained (solubilized intact zona pellucida glycoproteins, SIZP) was shown to be at least 95% pure by comparison to a reference standard of ZP using an ELISA assay.

ZP3 was purified from SIZP as described by Yurewicz et al (1987). ZP3 is one of three glycoproteins that make up the mealis zona pellucida. ZP3 is the major macromolecular component of the oocyte zona pellucida and has been shown to be the receptor for sperm.

Porcine ZP has been used to effect immunocontraception in a variety of mammals. Porcine ZP pellucida was used in the present studies for several reasons. Firstly, a comparison of the reactivity of ZP from five mammalian species to rabbit antiserum against porcine ZP indicated that pig ZP was recognized best followed by dog ZP while rat and cat ZP reacted poorly (Maresh, G. A. and B. S. Dunbar. 1987. Antigenic comparison of five species of mammalian zonae pellucida. J. Experimental Zoology 244: 299–307). Since seal and dog are closely related, (Berta, A., C. E. Rae, A. R. Wyss, 1989, "Skeleton of the oldest known pinniped Enaliarctos mealsi", Science 244: 60–62), anti-porcine ZP antibodies will bind to seal zonae. Secondly porcine ZP can also be easily obtained from slaughterhouse pigs. Thirdly, pigs ovulate multiple oocytes and thus provide a rich source of zona pellucida.

EXPERIMENT 1

Production of Anti-ZP Antibodies in Rabbits

Protocol.

Rabbits were injected i.m. (two rabbits for each treatment, details of each treatment are given in Table 1) as follows (a) ZP in three injections at monthly intervals, (b) ZP with Freund's complete adjuvant plus two boosters with ZP in Freund's incomplete adjuvant at 4 and 8 weeks and (c) ZP with muramyl dipeptide adjuvant (Sigma chemicals). In a second series, rabbits were immunized as above but ZP, plus adjuvant where applicable, were encapsulated in liposomes and in all cases in the second series only a single injection was administered. Preimmunization serum samples were taken from all rabbits. Titers of antibodies were measured by Elisa assay using both SIZP and ZP3 as antigen.

Results

The results of this study are illustrated in Table 1. Immunization of rabbits with ZP (no adjuvant) raised a low antibody titer after the third injection. A single injection of ZP in liposomes with no adjuvant raised no detectable antibodies. Use of muramyl dipeptide adjuvant did not stimulate antibody production regardless of being encapsulated in liposomes. Use of Freund's adjuvant stimulated antibody production to high levels after 69 days when the antigen was administered by 3 injections 4 weeks apart or as a single injection in liposomes. However, titers were higher using the former procedure. Measurement of antibodies directed specifically against ZP 3 indicated that antibody titers were similar after three injections without the use of liposomes as they were with a single injection with liposomes.

Therefore, these results indicate that a vaccine preparation containing ZP in combination with Freund's adjuvant and encapsulated into a liposome system can induce significant anti-ZP antibody levels for extended periods of time after a single injection.

TABLE 1

Effect of Encapsulating ZP in Liposomes on Anti-ZP Antibody Production in Rabbits

| Time (days) | Ag | Anti-ZP titer* | | | | | | | | | | |
|---|---|---|---|---|---|---|---|---|---|---|---|---|
| | | a | | b | | c | | | d | e | | f |
| PRE | SIZP | 0 | 0 | 0 | 0 | 0 | 0 | 0 | 0 | 0 | 0 | 0 | 0 |
| 27 | SIZP | 2 | 0 | 12 | 2 | 0 | 0 | 0 | 0.5 | 22 | 36 | 0 | 0.7 |
| 55 | SIZP | 12 | 3 | 96 | 68 | 2 | 1 | 0 | 0 | 50 | 50 | 0.3 | 0.6 |
| 69 | SIZP | 24 | 24 | 184 | 130 | — | — | — | — | 84 | 85 | — | — |
| 69 | ZP3 | 16 | 15 | 97 | 46 | — | — | — | — | 74 | 64 | — | — |

*A value of 100% indicates the serum being tested has the same titer as a pooled standard serum from rabbits rendered infertile by immunization with SIZP.

a - each rabbit was injected with SIZP (20 μg) in 0.5 ml saline.

b - each rabbit was injected first with SIZP (20 μg in a mixture of saline (0.25 ml) and Freund's complete adjuvant (0.25 ml) followed by two boosters of SIZP (20 μg) in a mixture of saline (0.25 ml) and Freund's incomplete adjuvant (0.25 ml).

c - each rabbit was injected with SIZP (20 μg) with muramyl dipeptide (5 μg) in saline (0.5 ml).

d - each rabbit was injected with SIZP (20 μg) encapsulated in soya lecithin liposomes containing phospholipon 90G (Nattermann Phospholipid Co., Cologne, Germany, 0.1 g), cholesterol (0.01 g) and saline (0.5 ml). Liposomes were prepared according to U.S. Pat. No. 4,485,054, which is incorporated herein by reference. Liposomal products containing ZP and adjuvants however can be prepared by many other methods presently known and used for manufacturing liposomes.

e - each rabbit was injected with SIZP (20 μg) encapsulated in liposomes as for d (0.25 ml) in Freund's complete adjuvant (0.25 ml).

TABLE 1-continued

Effect of Encapsulating ZP in Liposomes
on Anti-ZP Antibody Production in Rabbits

| Time | | | Anti-ZP titer* | | | |
|---|---|---|---|---|---|---|
| (days) Ag | a | b | c | d | e | f | f - each rabbit was injected with SIZP (20 µg) encapsulated in liposomes as for d (0.5 ml) containing muramyl dipeptide (5 µg).
PRE = preimmunization.

EXPERIMENT 2
Immunization of Captive Seals
Protocol.

Captive female grey seals (13) were divided into six groups of two animals each, except for group d which comprised three animals. The groups were immunized with a single injection i.m. as follows:

(a) ZP (15 µg) in liposomes with Freund's complete adjuvant (FCA)

(b) ZP (90 µg) in liposomes with FCA (c) ZP (90 µg) in FCA (d) ZP (90 µg) in liposomes with TITERMAX*

(e) ZP (90 µg) in TITERMAX (f) ZP (90 µg) in liposomes with BCG adjuvant in water All animals received in injection having a volume of 1.0 ml. Bacillus Calmette-Guerin or BCG is one component of FCA. Liposomes were formulated as previously described. TITERMAX (0.5ml) mixed with saline (0.5 ml) containing SIZP or liposomes (0.5 ml) containing SIZP as described by the manufacturer. TITERMAX (Cytrx Corporation, Norcross, Ga.) is a new adjuvant system which claims to induce higher titers of antibodies than FCA with a single injection while being less toxic to animals.

was greatest for groups (a) and (b) wherein zona pellucida was incorporated into a liposome system. Antibody titers were detected up until 22 months from immunization in the three seals from groups (a) and (b). (The fourth seal was returned to the wild at 11 months.) Without liposomes, group (c), antibody titers dropped off after 5 months. Substituting BCG for Freund's complete adjuvant was not effective in eliciting high titers (group f). The new adjuvant system, TITERMAX, was also not effective (groups (d) and (e)).

Therefore, the results of this study demonstrate that incorporation of the ZP and adjuvant into a liposome system results in a prolonged anti-ZP response after a single injection.

EXPERIMENT 3
Immunization of Harbour Seals

Twelve harbour seals, divided into three groups of four, were immunized with ZP in a single injection (Table 3). The seals were immunized immediately after giving birth. Samples were taken in the two or three week period until the seals left the pupping area. The results are shown in Table 3. Immunization (with 30 and 90 µg ZP) of harbour seals that had just given birth resulted in anti-ZP titers of only 9% (range 6 to 12%) of immunocontraceptive levels after 3 weeks. As discussed previously, anti-ZP antibodies can act

TABLE 2

Anti-ZP Antibody Production by Captive Seals.

Anti-ZP titer (% of standard serum)*
Time (months)

| Antigen | 1 | 2 | 3 | 4 | 5 | 6 | 7 | 8 | 9 | 10 | 11 | 12 | 13 | 16 | 18 | 20 | 22 |
|---|---|---|---|---|---|---|---|---|---|---|---|---|---|---|---|---|---|
| (a) ZP (15 µg) | 4 | 70 | 60 | 155 | 146 | 141 | 136 | 94 | 34 | 20 | — | — | — | — | — | — | — |
| FCA/liposomes | 3 | 92 | 166 | 216 | 192 | 182 | 224 | 185 | 150 | 117 | 135 | 95 | 87 | 23 | 35 | 20 | 18 |
| (b) ZP (90 µg) | 1 | 66 | 206 | 186 | 74 | 169 | 125 | 103 | 64 | 67 | 59 | 68 | 20 | 10 | 3 | 5 | 5 |
| FCA/liposomes | 18 | 78 | 230 | 227 | 230 | 247 | 223 | 164 | 127 | 122 | 115 | 74 | 31 | 14 | 10 | 7 | 4 |
| (c) ZP (90 µg) | 51 | 253 | 201 | 145 | 53 | | | | | | | | | | | | |
| FCA | 8 | 200 | 171 | 110 | 35 | | | | | | | | | | | | |
| (d) ZP (90 µg) | 3 | 16 | 9 | 2 | 1 | | | | | | | | | | | | |
| TITERMAX/ | — | 22 | 8 | 2 | 3 | | | | | | | | | | | | |
| liposomes | 25 | 28 | 20 | 7 | 2 | | | | | | | | | | | | |
| (e) ZP (90 µg) | 10 | 9 | 25 | 30 | 14 | 32 | — | — | — | — | — | | | | | | |
| TITERMAX | 3 | 36 | 22 | 59 | 7 | 20 | — | — | — | — | — | | | | | | |
| (f) ZP (90 µg) | 0.1 | 0.3 | 0.1 | 0.1 | 0 | — | — | — | — | — | — | | | | | | |
| BCG/liposomes | 0.4 | 0.2 | 0.1 | 0 | 0.1 | — | — | — | — | — | — | | | | | | |

ZP in this table indicates SIZP
* A value of 100% indicates the serum being tested has the same titer as a pooled standard serum from rabbits rendered infertile by immunization with SIZP.
— = no samples, seals returned to wild.

Results

The results of the immunization of the seals are shown in Table 2. The 1st and 2nd line of each group refers to results for two seals receiving the same treatment, that is, each formulation was tested in two seals, except for the ZP/TITERMAX/liposomes formulation which was tested in three seals. As can be seen from this table, the anti-ZP titer as an immunocontraceptive by inhibiting sperm penetration of ova or by inhibiting implantation of fertilized ova into the uterus. Since seals breed about 3 weeks after giving birth, it is possible that the above levels of anti-ZP antibodies would not affect sperm penetration of the oocytes. Immunization directly after giving birth may, however, have some effect on the implantation of the embryo since seals have a delayed implantation of up to three months.

TABLE 3

Production of anti-ZP antibodies by harbour seals immunized with ZP in a single injection at three doses

| ZP (μg) | Animal | Anti-ZP titer (expressed as a % of a standard serum)* Time (weeks) | |
|---|---|---|---|
| | | 2 | 3 |
| 15 | F | — | 5.9 |
| | F | 1.2 | 0.4 |
| | F | 0.7 | 2.7 |
| | F | 4.8 | — |
| 30 | F | 0.9 | — |
| | F | 1.8 | 6.5 |
| | F | — | 12.0 |
| | F | 18.0 | — |
| 90 | F | 1.1 | 6.9 |
| | F | 0.4 | — |
| | F | 4.7 | — |
| | F | 1.6 | 11.0 |

F = adult female
— = no sample
*A value of 100% indicates the serum being tested has the same titer as a pooled standard serum from rabbits rendered infertile by immunization with SIZP.

EXPERIMENT 4

Immunization of Grey Seals

Field studies of grey seals on Sable island have been conducted and are still in progress. Grey seals go to Sable island every year to have pups and breed and were therefore used in order to study the immunocontraceptive ability of the vaccine preparation. One group of female grey seals (approximately 100 animals) was immunized during the Jan. 1992 breeding season with liposomes in FCA (control) while the other group of 100 animals was immunized with ZP in liposomes in FCA. In Jan. 1993 the seals that returned to Sable Island were tested for anti-ZP titers. The results of this study are shown in Table 4. As expected, the control group of seals had antibody titers of zero. The experimental group, on the other hand, had appreciable titers. Providing anti-ZP titers persist for 1 year, it is expected that females in the experiment group will not conceive and therefore should not return to Sable Island in 1994.

It should also be noted that fewer seals in the experimental group returned to Sable Island during the 1993 season (51 of 85 expected) than the control group (76 of 85 expected). These results demonstrate that the liposome vaccine was effective as an immunocontraceptive even in the 1992 breeding season, immediately following administration of the vaccine. Anti-ZP antibodies inhibit implantation of embryos in the uterus. As seals have delayed implantation of about 3 months, antibody production had sufficient time to build up to concentrations which inhibited implantation (Henderson et al, 1988). This explanation is supported by recapture of three seals (#44, #65 and #66) which had been radio tracked. Their sera had anti-ZP titers of 12, 34 and 56%, respectively, 6 months after being immunized. The seals that return to Sable Island in 1994 will be further analyzed.

TABLE 4

Anti-ZP titers (as a % of a standard serum) in grey seals one year after injection with liposomes/FCA (controls) or ZP in liposomes/FCA (experimental)

| Controls | | Experimental | |
|---|---|---|---|
| Seal # | Titer (%) | Seal # | Titer (%) |
| 1 | 0 | 2 | 12 |
| 5 | 0 | 5 | 11 |
| 7 | 0 | 6 | 17 |
| 8 | 0 | 7 | 38 |
| 16 | 0 | 8 | 71 |
| 19 | 0 | 10 | 6 |
| 27 | 0 | 11 | 4 |
| 76 | 0 | 15 | 0 |
| 77 | 0 | 18 | 19 |
| 86 | 0 | 19 | 37 |
| 87 | 0 | 20 | 5 |
| 88 | 0 | 22 | 41 |
| 94 | 0 | 27 | 21 |
| 96 | 0 | 29 | 3 |
| 103 | 0 | 31 | 2 |
| 112 | 0 | 33 | 67 |
| 117 | 0 | 34 | 20 |
| | | 35 | 27 |
| | | 39 | 8 |
| | | 41 | 32 |
| | | 42 | 4 |
| | | 47 | 16 |
| | | 48 | 58 |
| | | 52 | 5 |
| | | 53 | 42 |
| | | 55 | 12 |
| | | 57 | 25 |
| | | 61 | 10 |
| | | 62 | 3 |
| | | 63 | 4 |
| | | 65 | 51 |
| | | 67 | 2 |
| | | 68 | 4 |
| | | 70 | 33 |
| | | 71 | 26 |
| | | 73 | 2 |
| | | 74 | 91 |
| | | 76 | 75 |
| | | 77 | 2 |
| | | 78 | 26 |
| | | 79 | 76 |
| | | 81 | 77 |
| | | 84 | 29 |
| | | 88 | 26 |
| | | 91 | 5 |
| | | 93 | 16 |
| | | 94 | 26 |
| | | 96 | 49 |
| | | 101 | 10 |
| | | 104 | 6 |

*A value of 100% indicates the serum being tested has the same titer as a pooled standard serum from rabbits rendered infertile by immunization with SIZP.

EXPERIMENT 5

After the filing of the priority application (U.S. Ser. No. 07/892,807), the inventors continued their research to develop and improve the previously mentioned liposomal vaccine formulations incorporating zona pellucida (ZP) antigens. One new embodiment involved the incorporation of a freeze-dried liposome containing ZP and adjuvant into a BALLISTIVET* biobullet. A biobullet is a gelatin capsule adapted to incorporate antigens for the purpose of vaccinating large animals. The biobullet is shot into the animal with a specially designed gun thus avoiding the need to restrain and inject the animals.

Procedure

1. Preparation of Biobullet

The biobullets were obtained from BALLISTIVET (Minneapolis, Minn.) and packed with the appropriate vaccine or control formulation as described below.

2. Immunization of Rabbits

Rabbits (two rabbits for each treatment) were injected i.m. (a+b below) or a biobullet was surgically implanted (c below) as follows: (a) ZP (20 µg) was encapsulated in liposomes prepared according to U.S. Pat. No. 4,485,054 and the liposomes were suspended in a mixture of saline (0.25 ml) and FCA (0.25 ml); (b) ZP (20 µg) encapsulated in liposomes prepared as above and suspended in a mixture of saline (0.25 ml) and FIA (0.25 ml) and (c) ZP (20 µg) encapsulated in liposomes prepared as above then freeze-dried and the freeze-dried powder suspended in FCA (0.25 ml). This suspension was packed into a biobullet (BallistiVet) and implanted i.m. by surgery.

Results:

The results of this study are shown in Table 5. Administration of ZP in liposomes with FCA produced high anti-porcine ZP antibody titers within one-two months. Replacing FCA with FIA, only marginally reduced anti-ZP antibody production. Use of freeze-dried liposomes with FCA in a biobullet resulted in an increased and prolonged production of anti-ZP antibodies.

TABLE 5

Effect of adjuvants on the production of anti-ZP antibodies by rabbits immunized with ZP in liposomes or freeze-dried liposomes in biobullets.

| Delivery/adjuvant | Titer (% of standard serum) Time (months) | | | | |
|---|---|---|---|---|---|
| | 1 | 2 | 3 | 4 | 5 |
| Liposome/FCA | 120 | 131 | 103 | 24 | 16 |
| | 38 | 38 | 24 | 17 | 19 |
| Liposome/FIA | 12 | 26 | 38 | 6 | — |
| | 91 | 97 | 73 | 18 | 19 |
| Biobullet/FCA | 159 | 149 | 215 | 27 | 66 |
| | 50 | 196 | 344 | 128 | 98 |

FCA = Freund's complete adjuvant.
FIA = Freund's incomplete adjuvant.

EXPERIMENT 6

In this experiment, the three seals from Experiment 2 in groups (a) and (b) that were tested up until month 22 for anti-ZP antibodies were given a booster of SIZP (90 µg) in freeze-dried liposomes with Freund's Incomplete Adjuvant (FIA) delivered with a BALLISTIVET biobullet into the hindquarter of each seal. Serum samples were taken after 4 weeks (month 23), 6 weeks (month 23.5), 8 weeks (month 24) and 12 weeks (month 25) after administration of the booster and anti-porcine ZP titers measured.

Results:

The results are shown in Table 6. A booster administered using a biobullet increased the anti-ZP antibodies to high levels which peaked 6–8 weeks later. It is expected that at least one more serum sample will be taken from these animals before they are released.

TABLE 6

| Antigen | Anti-ZP Titer (% of a standard serum) Time (months) | | | |
|---|---|---|---|---|
| | 23 | 23.5 | 24 | 25 |
| ZP (15 µg) | — | — | | |
| FCA/lipos | 116 | 159 | 119 | 79 |
| ZP (90 µg) | 54 | 59 | 68 | 33 |
| FCA/lipos | 15 | 21 | 41 | 13 |

EXPERIMENT 7

The zone pellucida (ZP) antigen used in the previously mentioned seal studies was porcine derived. Therefore in order to demonstrate that antibodies raised in seals to porcine ZP do cross-react with seal oocytes, the following experiment was conducted.

Procedure:

Antibodies from unimmunized harp seals and harp seals immunized with porcine ZP were purified by affinity chromatography using a Protein A column (Pierce Chemical Co., U.S.A.). The two antibody preparations were labelled ($^{14}$C) by reductive methylation (Jentoft, N. and D.G. Dearborn, 1979, Labelling of proteins by reductive methylation using sodium cyanoborohydride, J. Biol. Chem. 254: 4359–4365). Labelled antibodies were incubated with either seal or porcine oocytes overnight at 2° C. Unbound antibody was removed by centrifugation with washing (2×'s) with saline. Labelled antibody bound to oocytes was determined by liquid scintillation counting (LKB racbeta instrument). Oocytes were counted using a microscope and a haemocytometer-like counting chamber.

Results:

The results are shown in Table 7. Seal and porcine oocytes incubated with labelled antibodies from control seals bound only small quantities of antibody (25–52 DPM).

Seal oocytes (93) bound $^{14}$C-labelled anti-porcine ZP antibodies, 119 DPM (35.8 ng protein/oocyte) whereas porcine oocytes (96) bound more antibody (250 DPM; 72.9 ng protein/oocyte). This result suggests that about one-half the antibodies produced against porcine ZP in seals recognized and bound to seal ZP. Increasing the number of seal oocytes from 93 to 178 resulted in an increase in the quantity of antibody bound to oocytes (from 119 DPM to 169 DPM) demonstrating all sites on the seal oocytes capable of binding antibody were occupied. Increasing the number of porcine oocytes from 96 to 192, 432 and 864 oocytes resulted in no significant increase in the quantity of $^{14}$C-labelled antibody bound (250, 228, 236 and 277 DPM). This result demonstrated that 96 porcine oocytes bound all anti-porcine-ZP antibody present in the serum from the immunized seal.

These results verify that anti-porcine ZP antibodies bind to seal oocytes and provide evidence that immunocontraception may be explained by the binding of antibodies to the oocyte surface.

TABLE 7

Binding of $^{14}$C-labelled anti-ZP antibodies to pig and seal oocytes

| oocytes | | Ab from control seal | | Ab from immunized seal | |
|---|---|---|---|---|---|
| source | number | Ab bound (DPM) | Ab protein bound (ng/oocyte) | Ab bound (DPM) | Ab protein bound (ng/oocyte) |
| seal | 178 | 38 | 5.0 | 189 | 26.6 |
| seal | 93 | 25 | 6.3 | 119 | 35.8 |
| porcine | 864 | 52 | 1.4 | 277 | 9.0 |
| porcine | 432 | 47 | 2.6 | 236 | 15.3 |
| porcine | 192 | 45 | 5.5 | 228 | 33.3 |
| porcine | 96 | 55 | 13.6 | 250 | 72.9 |

The Ab from the control seal added to the oocytes contained 2124 DPM (specific activity, 42,309 DPM/mg protein) whereas the Ab from the immunized seal added to the oocytes contained 1672 DPM (specific activity, 35,685 DPM/mg protein).

SUMMARY

The above described experiments demonstrate that incorporating a zona pellucida antigen with a suitable adjuvant into a liposome delivery system results in an effective vaccine system for immunocontraception. The studies have shown that a single injection of the vaccine induces levels of anti-zona pellucida antibodies up to 22 months. A single injection vaccine is clearly advantageous for any immunocontraceptive protocol.

Initial studies have shown that incorporating a freeze-dried liposome containing the ZP antigen and adjuvant into a biobullet also induces high levels of anti-ZP antibodies in the seals. Such a delivery system is advantageous since it does not require that the animals be restrained to be injected with the vaccine.

While the above described experiments relate to certain embodiments of the present invention, it is to be appreciated that various modifications can be made to the vaccine composition without departing from the scope and spirit of the invention. For example, while the above described examples relate to porcine ZP3, any suitable and effective zona pellucida antigen, of porcine or other origin, may be employed. In fact, studies have shown that the genes that code for zona pellucida are conserved among mammals. The zona pellucida antigen may also be purified from oocytes or alternatively, a recombinant ZP antigen may be used. Modifications can also be made to the liposome delivery system. In particular, any liposomal system (such as freeze dried, liquid or semi-solid forms) which allows for the slow, controlled release of the antigen is considered within the scope of the present invention. Finally, the adjuvant used can also be modified, as long as it is effective in enhancing the immune response to the vaccine and is suitable for the intended application.

We claim:

1. A method of preventing fertilization in a mammal for at least twelve months which method consists of a single parenteral administration of an effective amount of a vaccine composition comprising a zona pellucida derived antigen and a Freund's adjuvant in a liposome formulation.

2. A method according to claim 1 wherein said zona pellucida derived antigen is ZP3.

3. A method according to claim 1 wherein said zona pellucida derived antigen is solubilized intact zona pellucida.

4. A method according to claim 1 wherein said zona pellucida derived antigen is porcine derived.

5. A method according to claim 1 wherein said liposome formulation is freeze-dried.

6. A method according to claim 1 wherin said mammal is a seal.

* * * * *